(12) United States Patent
Sulur et al.

(10) Patent No.: US 8,546,362 B2
(45) Date of Patent: Oct. 1, 2013

(54) MEDICINAL CREAM MADE USING NEOMYCIN SULPHATE, BETAMETHASONE VALERATE, AND CHITOSAN, AND A PROCESS TO MAKE THE SAME

(76) Inventors: Vanangamudi Subramaniam Sulur, Chennai (IN); Madhavan Srinivasan, Chennai (IN); Neelakandan Narayanan Chulliel, Chennai (IN); Haridas Sankar, Mumbai (IN); Kuppusamy Senthilkumar, Chennai (IN)

( * ) Notice: Subject to any disclaimer, the term of this patent is extended or adjusted under 35 U.S.C. 154(b) by 133 days.

(21) Appl. No.: 13/263,840

(22) PCT Filed: Apr. 5, 2010

(86) PCT No.: PCT/IB2010/051460
§ 371 (c)(1),
(2), (4) Date: Oct. 11, 2011

(87) PCT Pub. No.: WO2010/119364
PCT Pub. Date: Oct. 21, 2010

(65) Prior Publication Data
US 2012/0028942 A1 Feb. 2, 2012

(30) Foreign Application Priority Data
Apr. 13, 2009 (IN) .......................... 945/MUM/2009

(51) Int. Cl.
A61K 31/56 (2006.01)
(52) U.S. Cl.
USPC ........................................ 514/171

(58) Field of Classification Search
USPC ....................................................... 514/171
See application file for complete search history.

(56) References Cited

U.S. PATENT DOCUMENTS

| 3,764,616 A | 10/1973 | Elks et al. |
| 2003/0206958 A1 | 11/2003 | Cattaneo et al. |

FOREIGN PATENT DOCUMENTS

| DE | 10 2006 049585 | 4/2008 |
| EP | 0 368 253 | 5/1990 |

*Primary Examiner* — Raymond Henley, III (57) ABSTRACT

The present invention is directed to a composition for treating bacterial skin infections & skin inflammation, along with skin rejuvenation. More particularly, the present invention relates to a pharmaceutical cream comprising a biopolymer, a corticosteroid and an antibacterial active ingredient. It discloses a composition for treating bacterial skin infections & skin inflammation, along with skin rejuvenation containing a) a biopolymer in the form of chitosan, b) a combination of active pharmaceutical ingredients (APIs), neomycin sulphate & betamethasone valerate used in treating bacterial skin infections & skin inflammations, c) a cream base containing primary and secondary emulsifiers, waxy materials, co-solvents, acids, preservatives, buffering agents, anti oxidants, chelating agents, and humectants and d) water. The active ingredients, namely chitosan, a corticosteroid Betamethasone Valerate, and an antibacterial agent Neomycin Sulphate, are incorporated in cream base for use in treating bacterial skin infections and skin inflammation due to allergy & itching, & wounds on human skin involving contacting human skin with the above identified composition.

9 Claims, 1 Drawing Sheet

MEDICINAL CREAM MADE USING NEOMYCIN SULPHATE, BETAMETHASONE VALERATE, AND CHITOSAN, AND A PROCESS TO MAKE THE SAME

FIELD OF INVENTION

The present invention relates to a composition for treating bacterial skin infections & skin inflammation, along with skin rejuvenation. More particularly, the present invention relates to a pharmaceutical cream comprising a biopolymer, a corticosteroid in the form of Betamethasone Valerate and an antibacterial agent in the form of Neomycin Sulphate as the starting Active Pharmaceutical Ingredient (API).

BACKGROUND OF THE INVENTION

Skin disorders can be broadly categorized as those arising from bacterial forms or fungi. Antifungal or antibacterial compositions are traditionally applied as lotions, creams or ointments. Furthermore in many instances, it is difficult to ascertain whether the skin condition is due to a bacterial agent or a fungus.

One approach to treating skin disorders is through elimination by trial and error. Antibacterial or antifungal compositions are applied in turn and response monitored and treatment modified. A major disadvantage of this approach is that treatment needs to be applied many times a day during the treatment period. This is greatly inconvenient and also not cost effective for a majority of human population, particularly in the under-developed nations.

There are several treatments available to treat skin disorders caused by bacteria or fungi. Typically, such compositions use steroids, antibacterial agents or antifungal agents, (or a fixed dose combination of these) and focus on these pharmaceutically active ingredients. The composition of such formulations is such as to enhance their physical/chemical/bio-release profile.

Many skin disorders caused by inflammation and bacterial attacks lead to itching and subsequent scratching, which, among other causes, can in turn lead to serious and complicated secondary infections. The conventionally available treatments do not focus on skin healing or rejuvenation; normally these two aspects are left to heal naturally.

The word healing as related to compromised skin conditions (cuts, wounds, infections, inflammations, abrasions, etc.) are not only about prevention, control, elimination of the source cause such as bacteria or fungi but also to restore the skin to its pre-infection state.

The current approaches of skin treatment can be broadly categorized into two stages, a. healing b. restoration of skin to pre-ailment state. The healing part comprises elimination, to the best possible extent, of the root cause of the disorder. This may be elimination of bacteria or fungi causing the infection through a suitable treatment of antibacterial or antifungal agents or reducing the inflammation through steroid treatment. While this treatment is under way, the ongoing compromised condition of the skin continues to be susceptible to secondary infections which can be of quite serious nature. In the case of scratched or wounded skin, it is important for blood clotting to occur quickly as it reduces chances of secondary infections. The focus of such treatments, which are administered through creams, lotions, ointments is on the action of active pharmaceutical ingredients. Cream bases or ointment bases are merely viewed as carriers to take APIs to the sites of disorder.

However, the aspect of restoring the skin back to its pre-disorder state is almost completely left to nature. Therefore one key drawback of the existing skin treatment approaches is that they run the risk of secondary infections due to slow blood clotting and wound healing process.

Furthermore, from the study of the prior art several lacking aspects of the existing prescription derma products used for topical treatment of skin disorders. This is manifested by the fact that the cream base matrix or the ointment base has been overlooked for any potential therapeutic benefits. In particular none of the available prior art suggests that:

Topical skin formulations can deliver skin healing or regeneration beyond the activity of the main APIs such that the therapeutic outcome of the main APIs is enhanced.

The addition of biologically active polymers (the so-called biopolymers) is a complex process in which the stability of the formulations could be compromised if the right biopolymer or naturally interacting formulation excipients or process parameters are not well thought through and optimized to enhance and complement therapy outcomes at the drug design stage itself.

Incorporation of a functionally bio-active excipient polymer in cream matrix while retaining the functional stability of the API in a single dose format of dermaceutical cream involves resolution of problems specific to the physical stability of cream matrix.

A look at some of the existing patents illustrates the above points.

First, U.S. Pat. No. 487,775 relates to polymeric aminosaccharides, processes for their preparation and their use as antihypercholesterolemic agents. More particularly, it relates to polymeric aminosaccharides which are high molecular weight nonabsorbable resins resulting from the cross linking of monomeric or polymeric aminosaccharides and dialdehydes via Schiff's base formation followed by reductive amination to give non-hydrolyzable linkages.

U.S. Pat. No. 4,013,792 discloses a clear gel composition containing a topically active anti-inflammatory steroid and a neomycin salt. The clear gel composition is prepared by dissolving the steroid in a polyhydroxy alcohol/lower alcohol solvent, a major proportion of the polyhydroxy alcohol solvent being propylene glycol, and adding a hydroxycellulose ingredient; an aqueous solution of the neomycin salt is then added to the steroid formulation and, upon the addition of an alkali metal chloride salt, such as sodium chloride, a clear gel is obtained. The pH may be adjusted to 4-5. The resulting composition is indicated for the relief of corticosteroid-responsive dermatoses.

U.S. Pat. No. 4,740,372 discloses a composition for the treatment of psoriasis vulgaris, and a method for its preparation are described. The compound is made from cortocosteroids; salicylic acid; tetracycline chloride; gentamycin sulfate; neomycin sulfate; trypsin; chymotrypsin; and bismuth. And available in a neutral cream, ointment, etc., at which time it is ready for use. This composition of ingredients acting together apparently achieves good results in the treatment psoriasis vulgaris.

None of the above mentioned patent applications teach or suggest:

Use of the cream base matrix as a functional element of the cream rather than a mere carrier for the main APIs Use a known bio-polymer as a functional excipient along with anti bacterial agent Neomycin Sulphate, and a steroid, Betamethasone Valerate Providing far superior healing effects as micro-film forming, blood clotting, supporting epidermal growth, microbial electrostatic immobilization take effect simultaneously rather than one after the other as would be the case in conventional single-drug therapy Improve overall medicinal properties of the cream, complimenting the API used in the cream matrix There is therefore a need for a single-dose multiple API topical treatment that will be provided in a cream base, which cream base provides therapeutical value complementary to that provided by the main APIs and serves the purpose over and above that of being a mere carrier or delivery mechanism.

OBJECTS AND ADVANTAGES OF THE INVENTIONS

There is therefore a need to provide a single dose Neomycin Sulphate & Betamethasone Valerate topical treatment formulation that will provide an effective treatment against bacterial infections, skin inflammations and also help actively heal the skin rejuvenate.

Further objects of the present invention are to provide topical skin treatment formulations that:

Can deliver skin healing or regeneration beyond the activity of the main APIs—Neomycin Sulphate & Betamethasone Valerate such that the therapeutic outcomes of the main APIs are enhanced.

Contain biologically active polymers (the so-called biopolymers) without compromising the stability of the formulations could be compromised if the right biopolymer is not selected.

Incorporate a functionally bio-active excipient polymer in cream matrix while retaining the functional stability of the APIs in a single dose format

SUMMARY OF THE INVENTION

The present invention is directed to a composition for treating bacterial skin infections & skin inflammation, along with skin rejuvenation containing a) A biopolymer in the form of Chitosan b) A combination of active pharmaceutical ingredients (APIs), Neomycin Sulphate & Betamethasone Valerate used in treating bacterial skin infections & skin inflammations, c) A cream base containing primary and secondary emulsifiers, waxy materials, co-solvents, acids, preservatives, buffering agents, anti oxidants, chelating agents, and humectants.

d) Water

The active ingredients, namely chitosan, a corticosteroid Betamethasone Valerate, and an antibacterial agent Neomycin Sulphate, are incorporated in cream base for use in treating bacterial skin infections and skin inflammation due to allergy & itching, & wounds on human skin involving contacting human skin with the above identified composition.

DETAILED DESCRIPTION OF THE INVENTION

Other than in the operating examples, or where otherwise indicated, all numbers expressing quantities of ingredients are understood as being modified in all instances by the term "about".

The present invention provides a uni-dose multi-API Neomycin Sulphate & Betamethasone Valerate formulation for topical skin treatment in the field of prescription medicaments. The prescription medication is distinct in its use as compared with the so-called cosmeceuticals. The cosmeceuticals are aimed towards beautification or betterment of a more-or-less intact skin or of a skin not suffering from a serious disorder. On the other hand, prescription skin formulations are aimed to provide treatment for serious skin disorders resulting from infections and wounds.

From the study of the prior art several lacking aspects of the existing topical treatment formulations in the field of prescription medications are evident. The prior art does not teach or suggest that:

Topical skin formulations can deliver skin healing or regeneration beyond the activity of the main APIs such that the therapeutic outcomes of the main APIs are enhanced.

The addition of biologically active polymers (the so-called biopolymers) is a complex process in which the stability of the formulations could be compromised if the right biopolymer is not selected.

Incorporation of a functionally bio-active excipient polymer in cream matrix while retaining the functional stability of the API in a single dose format of dermaceutical cream involves resolution of problems specific to the physical stability of cream matrix.

The active compounds Neomycin Sulphate, Betamethasone Valerate which may be employed in the present invention are well known in the art of treatment of bacterial infections, skin inflammations respectively and a bio polymer for treating wounds and rejuvenating human skin involving contacting human skin with the above identified composition.

Examples of suitable biopolymer, which may be used, include, but are not limited to chitosan and the like.

Examples of suitable topical Corticosteroids, which may be used, include, but are not limited to, Betamethasone Valerate, Betamethasone dipropionate, Beclomethasone dipropionate, Clobetasol propionate, Clobetasone butyrate, Halobetasol propionate, Mometasone furoate, Halcinonide, Fluocinonide, Triamcinolone acetonide, Fluticasone propionate, Amcinonide, Diflorasone diacetate, Prednicarbate, Hydrocortisone acetate and the like.

Examples of suitable topical antibacterial agents, which may be used, include, but are not limited to Neomycin Sulphate, Sodium Fusidate, Calcium Mupirocin, Gentamycin, Silver Sulphadiazine, Ciprofloxacin, Framycetin Sulphate, Quinidochlor, Povidone-Iodine, Sisomicin, Nitrofural and the like.

This active compounds Neomycin Sulphate & Betamethasone Valerate require a base component to be used in the pharmaceutical composition that uses the compounds, since the compounds cannot, by themselves, be deposited directly on to human skin due to their harshness.

The base component usually contains primary and secondary emulsifiers, waxy materials, co-solvents, acids, preservatives, buffering agents, anti oxidants, chelating agents, humectants and the like.

Chitosan

Chitosan is a linear polysaccharide composed of randomly distributed β-(1-4)-linked D-glucosamine (deacetylated unit) and N-acetyl-D-glucosamine (acetylated unit). It is known to have a number of commercial uses in agriculture and horticulture, water treatment, chemical industry, pharmaceuticals and biomedics.

It's known properties include accelerated blood clotting. However, it is not known to a person skilled in the art that chitosan's behaviour with a pharmaceutical active ingredient such as an antibacterial or antifungal agent needs to be treated with caution.

It is known to have film forming, mucoadhesive and viscosity-increasing properties and it has been used as a binder and disintegrating agent in tablet formulations.

Chitosan generally absorbs moisture from the atmosphere/environment and the amount absorbed depends upon the initial moisture content, temperature and relative humidity of the environment.

It is regarded as a non-toxic and non-irritant material. It is biocompatible with both healthy and infected skin and has been shown to be biodegradable as it is derived from shrimps, squids and crabs.

Chitosan due to its unique physical property accelerates wound healing and wound repair. It is positively charged and soluble in acidic to neutral solution. Chitosan is bioadhesive and readily binds to negatively charged surfaces such as mucosal membranes. Chitosan enhances the transport of polar drugs across epithelial surfaces. Chitosan's properties allow it to rapidly clot blood, and it has recently gained approval in the USA for use in bandages and other hemostatic agents.

Chitosan is nonallergenic, and has natural anti-bacterial properties, further supporting its use. As a micro-film forming biomaterial, chitosan helps in reducing the width of the wound, controls the oxygen permeability at the site, absorbs wound discharge and gets degraded by tissue enzymes which are very much required for healing at a faster rate. It also reduces the itching by providing a soothing effect. It also acts like a moisturizer. It is also useful in treatment of routine minor cuts and wounds, burns, keloids, diabetic ulcers and venous ulcers. Chitosan used in the present invention comes in various molecular weights ranging from 1 kdal to 5000 kdal.

Chitosan is discussed in the US Pharmacopoeia forum with regard to its functional excipient category. Since chitosan is basically a polymer, it is available in various grades depending upon the molecular weight. The various grades of chitosan include chitosan long chain, chitosan medium chain & chitosan short chain. The grades long, medium & short chain directly corresponds to the molecular weight of the chitosan.

Generally the long chain grade has a molecular weight in the range of 500,000-5,000,000 Da, the medium chain grade has a molecular weight in the range of 1,00,000-2,000,000 Da and the short chain grade has a molecular weight in the range of 50,000-1,000,000 Da.

The molecular weight of the chitosan plays an important role in the formulation. Higher molecular weight chitosan imparts a higher viscosity to the system and lower molecular weight chitosan imparts a lower viscosity to the system. However the medium chain grade chitosan delivered an optimum level of viscosity to the formulation. Since the dosage form is a cream, appropriate levels of viscosity is required to achieve a good spreadability over the skin.

The inventors finalized the chitosan medium chain grade for the present invention since it imparted the required rheologic properties to the cream without compromising the therapeutic activity of both the actives Neomycin Sulphate & Betamethasone Valerate and chitosan. The concentration of chitosan medium chain grade was carefully arrived based on several in house trials and Preclinical animal studies for efficacy.

Topical Corticosteroids

Topical corticosteroids are a powerful tool for treating skin diseases. Corticosteroids include drugs such as Betamethasone Valerate, Betamethasone dipropionate, Beclomethasone dipropionate, Clobetasol propionate, Clobetasone butyrate, Halobetasol propionate, Mometasone furoate, Halcinonide, Fluocinonide, Triamcinolone acetonide, Fluticasone propionate, Amcinonide, Hydrocortisone acetate, Diflorasone diacetate, Prednicarbate, etc.

Topical corticosteroids are classified by their potency, ranging from weak to extremely potent. They include weak potent steroids, moderate potent steroids, potent steroids, very potent steroids and extremely potent steroids. The high potency steroids include Betamethasone Dipropionate, Betamethasone Valerate, Diflorasone Diacetate, Clobetasol Propionate, Halobetasol Propionate, Desoximetasone, Diflorasone Diacetate, Fluocinonide, Mometasone Furoate, Triamcinolone Acetonide, etc. Low potency topical steroids include Desonide, Fluocinolone acetate, and Hydrocortisone acetate, etc.

Topical corticosteroid is indicated for the relief of the inflammatory and pruritic manifestations of corticosteroid responsive dermatoses.

Betamethasone Valerate

Betamethasone is a moderately potent glucocorticoid steroid with anti-inflammatory and immunosuppressive properties. Unlike other drugs with these effects, betamethasone does not cause water retention. It is applied as a topical cream, ointment, foam, lotion or gel to treat itching (e.g. from eczema). Betamethasone sodium phosphate is sometimes prescribed as an intramuscular injection (I.M) for itching from various ailments including allergic reactions to poison ivy and similar plants.

The compound is available as a number of ester derivatives: Dipropionate (branded as Diprosone, Diprolene and others), Sodium Phosphate and Valerate (branded as Betnovate, Celestone and others).

Betamethasone Valerate is chemically designated as 9-Fluoro-11β, 17,21-trihydroxy-16β-methylpregna-1,4-diene-3,20-dione 17-valerate. The molecular formula and weight of Betamethasone Valerate are C27H37FO6 and 476.58 respectively. 1.2 mg of Betamethasone Valerate is equivalent to 1.0 mg Betamethasone. The topical corticosteroids constitute a class of primarily synthetic steroids and are used as anti-inflammatory and antipruritic agents.

Betamethasone Valerate is a white to practically white, odorless powder. It melts at 190° C. with decomposition. It is practically insoluble in water, freely soluble in acetone and in chloroform, soluble in alcohol, and slightly soluble in benzene and in ether.

Pharmacology & Mechanism of Action

Betamethasone Valerate as a topical corticosteroid, has anti-inflammatory, antipruritic and vasoconstrictive actions. The mechanisms of anti-inflammatory activity of the topical corticosteroids are unclear. Various laboratory methods, including vasoconstrictor assay, are used to compare and predict potencies and/or clinical efficacies of the topical corticosteroids. There is some evidence to suggest that a recognizable correlation exists between vasoconstrictor potency and therapeutic efficacy in man. The exact mechanism of anti-inflammatory action of Betamethasone Valerate is unknown, but however it produces multiple glucocorticoid and mineralocorticoid effects.

Pharmacokinetics

The extent of percutaneous absorption of topical corticosteroids is determined by many factors including the vehicle, the integrity of the epidermal barrier, and the use of occlusive dressings. Topical corticosteroids can be absorbed from normal intact skin. Inflammation and/or other disease processes in the skin increase percutaneous absorption. Occlusive dressings substantially increase the percutaneous absorption of topical corticosteroids. Thus, occlusive dressings may be a valuable therapeutic adjunct for treatment of resistant dermatoses. Once absorbed through the skin, topical corticosteroids are handled through pharmacokinetic pathways similar to systemically administered corticosteroids. Corticosteroids are bound to plasma proteins in varying degrees. Corticosteroids are metabolized primarily in the liver and are then excreted by the kidneys. Some of the topical corticosteroids and their metabolites are also excreted into the bile.

Indications

Betamethasone Valerate is indicated for the relief of the inflammatory and pruritic manifestations of corticosteroid-responsive dermatoses.

Topical Anti-bacterial:

Topical Anti-bacterial is intended to target skin for bacterial infections caused by *Staphylococcus aureus, Staphylococcus epidermidis*, Methicillin Resistance *Staphylococcus Aureus* (MRSA) etc.

Anti-bacterial act by inhibiting cell wall synthesis by combining with bacterial ribosomes and interfering with mRNA ribosome combination.

In another hypothesis it is believed that anti-bacterial induce ribosomes to manufacture peptide chains with wrong amino acids, which ultimately destroy the bacterial cell.

Topical antibacterial agents include, but are not limited to, Neomycin Sulphate, Sodium Fusidate, Calcium Mupirocin, Gentamycin, Silver Sulphadiazine, Ciprofloxacin, Framycetin Sulphate, Quinidochlor, Povidone-Iodine, Sisomicin, Nitrofural and the like.

Neomycin Sulphate

Neomycin, an aminoglycoside antibiotic obtained from cultures of *Streptomyces fradiae*, is a complex of 3 components with various degrees of antimicrobial activity—neamine, neomycin B, and neomycin C. The commercially available drug is comprised almost entirely of the sulfate salt of neomycin B and occurs as a white to slightly yellow, hygroscopic powder or cryodesiccated solid and is freely soluble in water and very slightly soluble in alcohol.

It is used to treat bacterial infections, by killing or stopping the growth of the bacteria responsible.

The molecular formula of Neomycin sulphate is $C_{23}H_{46}N_6O_{13}*H_2SO_4$, and the molecular weight is 908.9. The chemical name is (1S-(1a,4a,5b,5a))-1,5,6-Trideoxy-4-O-beta-D-glucopyranosyl-5-(hydroxymethyl)-1-((4,5,6-trihydroxy-3-(hydroxymethyl)-2-cyclohexen-1-yl)amino)-D-chiro-inositol.

Pharmacology & Mechanism of Action

Neomycin sulphate is active against *Staphylococcus aureus, Escherichia coli, Haemophilus influenzae, Klebsiella-Enterobacter* species, *Neisseria* species. In general, neomycin is active against many aerobic gram-negative bacteria and some aerobic gram-positive bacteria. The drug is inactive against fungi, viruses, and most anaerobic bacteria.

In vitro, neomycin concentrations of 1-12.5 mcg/ml inhibit most susceptible strains of *Escherichia coli, Haemophilus influenzae, Moraxella lacunata*, indole-positive and indole-negative *Proteus, Staphylococcus aureus, S. epidermidis*, and *Serratia*. However, different species and different strains of the same species may exhibit wide variations in susceptibility in vitro. In addition, in vitro susceptibility does not always correlate with in vivo activity. Neomycin is only minimally active against streptococci. *Pseudomonas aeruginosa* is generally resistant to the drug.

Neomycin is usually bactericidal in action. Although the exact mechanism of action has not been fully elucidated, the drug appears to inhibit protein synthesis in susceptible bacteria by irreversibly binding to 30S ribosomal subunits.

Pharmacokinetics

Neomycin sulfate is not absorbed following topical application to intact skin; however, the drug is readily absorbed through denuded or abraded areas of skin or skin that has lost the keratin layer as in wounds, burns, or ulcers. Neomycin is rapidly absorbed from the peritoneum, draining sinuses, wounds, or surgical sites; use of large doses at these sites may result in substantial plasma concentrations of the drug.

Indications

Neomycin is used topically in combination with other anti-infectives for the prevention or treatment of superficial infections of the skin caused by susceptible bacteria. Although minor skin infections and wounds usually heal without treatment, some minor skin wounds do not heal without therapy and it is impossible to determine at the time of injury which wounds will be self-healing. Therefore, some experts believe that, by reducing the number of superficial bacteria, topical anti-infectives are useful for preventing infection in minor skin injuries (e.g., cuts, scrapes, bums). The role, if any, of most topical anti-infectives for the treatment of superficial skin infections has not been fully elucidated, and systemic anti-infective therapy is required for the treatment of serious or extensive skin infections. Therefore, self-medication with topical anti-infectives for the treatment of superficial skin infections currently is not recommended. In addition, some clinicians caution that indiscriminate use of topical neomycin may result in the emergence of organisms resistant to the drug and other aminoglycosides. Neomycin is used topically in fixed-combination with corticosteroids and other anti-infectives for the treatment of corticosteroid-responsive dermatoses with secondary infection.

Most of the topical products are formulated as either creams or ointments. A cream is a topical preparation used for application on the skin. Creams are semi-solid emulsions, which are mixtures of oil and water in which APIs (Active Pharmaceutical Ingredients) are incorporated. They are divided into two types: oil-in-water (O/W) creams which compose of small droplets of oil dispersed in a continuous water phase, and water-in-oil (W/O) creams which compose of small droplets of water dispersed in a continuous oily phase. Oil-in-water creams are user-friendly and hence cosmetically acceptable as they are less greasy and more easily washed with water. An ointment is a viscous semisolid preparation containing APIs, which are used topically on a variety of body surfaces. The vehicle of an ointment is known as ointment base. The choice of a base depends upon the clinical indication of the ointment, and the different types of ointment bases normally used are:

Hydrocarbon bases, e.g. hard paraffin, soft paraffin

Absorption bases, e.g. wool fat, bees wax

Both above bases are oily and greasy in nature and this leads to the undesired effects like difficulty in applying & removal from the skin. In addition this also leads to staining of the clothes. Most of the topical products are available as cream formulation because of its cosmetic appeal.

The acidic scale of pH is from 1 to 7, and the base scale of pH is from 7 to 14. Human skins pH value is some where between 4.5 and 6. Newborn baby's skin pH is closer to neutral (pH 7), but it quickly turns acidic. Nature has designed this probably to protect young children's skin, since acidity kills bacteria. As people become older, the skin becomes more and more neutral, and won't kill as many bacteria as before. This is why the skin gets weak and starts having problems. The pH value goes beyond 6 when a person actually has a skin problem or skin disease. This shows that it is necessary to choose topical that have a pH value close to that of skin of a young adult.

A slight shift towards the alkaline pH would provide a better environment for microorganisms to thrive. Most of the topical products are available as creams. Active compounds in cream formulations are available in ionized state, whereas in case of ointments these are present in non-ionized state. Generally, the cream formulations are the first choice of the formulators in design and development of topical dosage forms, as the cream formulations are cosmetically elegant, and also as the active compound is available in ionized state, and the drug can penetrate the skin layer fast which makes the formulation totally patient friendly.

The pH of the cream of the present invention with a functional biopolymer such as chitosan with Neomycin Sulphate & Betamethasone Valerate is from about 3 to 6. On the other hand, ointments that are commercially available are greasy and cosmetically non elegant. Furthermore, as the active compound in an ointment is in non-ionized form, the penetration of skin is slow.

It is essential that the active drug penetrates the skin for the optimum bio-dermal efficacy. The particle size of the active drug plays an important role here. It is necessary that the active drug is available in colloidal or molecular dispersed state for the product being highly efficacious form. Also this is to be achieved in the safe pH compatible environment of skin (4.0 to 6.0). To achieve all these, it is essential to choose proper vehicles or co-solvents for the dissolution or dispersion of the drug. The product of the present invention is highly efficacious due to the pronounced antibacterial/anti-inflammatory & wound healing activity of the active ingredients Neomycin Sulphate & Betamethasone Valerate, which are available in ultra micro-size, colloidal form, which enhances skin penetration.

Rationale for Neomycin Sulphate & Betamethasone Valerate and Chitosan Combination:

Numerous topical treatments are currently employed for the treatment of bacterial infections and skin inflammations. However there is no effective single-dose therapy for protecting the skin, controlling superficial bleeding, wounds and burns. To meet this need and to bring affordable and safe therapy to the dispersed segment of population across all countries/communities, a therapy with unique combination of chitosan, a biopolymer with skin rejuvenation properties with Neomycin Sulphate & Betamethasone Valerate is proposed as a novel cream.

Topical Neomycin Sulphate have profound efficacy in primary & secondary bacterial skin infections of varied etiology due to its antibacterial properties. A drawback of the monotherapy with topical antibacterial like Neomycin Sulphate has been the relatively slow onset of the effect.

Steroids like Betamethasone Valerate provide much wanted rapid relief of the pruritus. Combining Neomycin Sulphate with topical Betamethasone Valerate is expected to provide fast relief because of the steroid effect and a lingering post treatment antibacterial effect allowing for an overall reduction in intermittent use of the product. Generally topical steroids of high potency are used for duration of one to two weeks; for low potency steroids the period may be three to four weeks.

By employing Betamethasone Valerate, Neomycin Sulphate & chitosan in a formulation, the properties of steroids, antibacterial and chitosan are optimized. As chitosan is film forming, biocompatible, non-allergenic material it helps in protecting the skin by acting as a barrier. It further controls the superficial bleeding caused by scratching and also arrests the mobility of pathogens due to its cationic charge.

The properties of Betamethasone Valerate, Neomycin Sulphate and chitosan's skin regenerative aspects are well exploited in the present invention and the maximum therapeutic benefit is passed on to the patient thereby aiding in faster healing. This ensures that the patient would benefit for the treatment of skin dermatitis, eczema, wounds, and burns with bacterial infections.

The inclusion of chitosan in the formulation takes care of many attributes, which are considered to be very much essential in treating skin ailments. The combination of chitosan with Betamethasone Valerate and Neomycin Sulphate is unique and novel since this is not available commercially across the globe.

The concept of the combination is justified by considering the physical, chemical and therapeutic properties of chitosan used in combination with Betamethasone Valerate, Neomycin Sulphate.

Inventive Aspects of the Present Invention:

Another inventive aspect of the present invention is that the addition of a functional excipient in the cream base is not a straight forward process of mere addition. The inventor has found that the compatibility of the functional excipient such as chitosan with other agents in the cream is of critical importance. This is because incompatibility would compromise the stability of the final product. As examples, the inventors have found that well known excipients such as Xanthan Gum and carbomer which have been variously used as stabilizing agents, cannot be used in combination with functional biopolymers such as chitosan.

Excipients for topical dosage forms include Polymers, Surfactants, Waxy Materials, and Emulsifiers etc. Polymers are used as gelling agents, suspending agents, viscosity builders, release modifiers, diluents, etc. Surfactants are used as wetting agents, emulsifiers, solubilising agents release enhancers, etc.

Generally Polymers & Surfactants may or may not possess ionic charge. They may be anionic or cationic or non-ionic in nature. If anionic excipients are included in the formulation they interact with cationic formulation excipients and produce products which are not homogenous, aesthetically not appealing and give rise to unwanted by products, possible allergens, impurities, toxic substances etc due to incompatibility.

Since the dosage is for the treatment of ailing patients, these incompatibilities in the products cannot be accepted and these add more complication to the patients.

The inventors carefully screened the excipients which included the Polymers and Surfactants for developing a formulation. A thorough study was performed after screening the short listed excipients. The possible interactions between the excipients were given much focus and detailed experiments were done.

To quote some examples about the anionic-cationic interaction in the cream dosage form the inventors made some formulations of Betamethasone Valerate and Neomycin Sulphate (see tables 1-5) containing Xanthan Gum & Chitosan, Acrylic acid polymer & Chitosan, Sodium Lauryl Sulphate & Chitosan, Docusate Sodium & Chitosan and Gum Arabic & Chitosan. The results clearly indicated the occurrence of interactions which was very much visible and seen as lumps into the entire system. The final product was also not aesthetically appealing without homogeneity. The attached FIG. 1 clearly explains the interaction between chitosan and unsuitable anionic excipients. Based on the observations and thorough knowledge about the excipients, the inventors arrived at a robust formula without any possible interactions.

TABLE 1

Formulation of Neomycin Sulphate & Betamethasone Valerate Cream with Chitosan and Xanthan Gum

| S. No | Ingredients | % w/w |
|---|---|---|
| 1 | Neomycin Sulphate | 0.5 |
| 2 | Betamethasone Valerate | 0.12 |
| 3 | Xanthan Gum | 1 |
| 4 | Chitosan | 0.25 |
| 5 | Lactic acid | 0.1 |
| 6 | Cetostearyl Alcohol | 8.25 |
| 7 | White Soft Paraffin | 8.25 |
| 8 | Polyoxyl 20cetostearyl ether (Cetomacrogol 1000) | 2.5 |
| 9 | Light Liquid Paraffin | 5 |
| 10 | Isopropyl Myristate | 5 |
| 11 | Propylene Glycol | 10 |
| 12 | Methyl Paraben | 0.2 |
| 13 | Propyl Paraben | 0.02 |
| 14 | Disodium Edetate | 0.1 |
| 15 | Disodium hydrogen Orthophosphate anhydrous | 0.5 |
| 16 | Purified Water | 58.5 |

TABLE 2

Formulation of Neomycin Sulphate & Betamethasone Valerate Cream with Chitosan and Acrylic Acid Polymer

| S. No | Ingredients | % w/w |
|---|---|---|
| 1 | Neomycin Sulphate | 0.5 |
| 2 | Betamethasone Valerate | 0.12 |
| 3 | Acrylic Acid Polymer | 0.75 |
| 4 | Chitosan | 0.25 |
| 5 | Lactic acid | 0.1 |
| 6 | Cetostearyl Alcohol | 8.25 |
| 7 | White Soft Paraffin | 8.25 |
| 8 | Polyoxyl 20cetostearyl ether (Cetomacrogol 1000) | 2.5 |
| 9 | Light Liquid Paraffin | 5 |
| 10 | Isopropyl Myristate | 5 |
| 11 | Propylene Glycol | 10 |
| 12 | Methyl Paraben | 0.2 |
| 13 | Propyl Paraben | 0.02 |
| 14 | Disodium Edetate | 0.1 |
| 15 | Disodium hydrogen Orthophosphate anhydrous | 0.5 |
| 16 | Purified Water | 58.5 |

TABLE 3

Formulation of Neomycin Sulphate & Betamethasone Valerate Cream with Chitosan and Sodium Lauryl Sulphate

| S. No | Ingredients | % w/w |
|---|---|---|
| 1 | Neomycin Sulphate | 0.5 |
| 2 | Betamethasone Valerate | 0.12 |
| 3 | Sodium Lauryl Sulphate | 1 |
| 4 | Chitosan | 0.25 |
| 5 | Lactic acid | 0.1 |
| 6 | Cetostearyl Alcohol | 8.25 |
| 7 | White Soft Paraffin | 8.25 |
| 8 | Polyoxyl 20cetostearyl ether (Cetomacrogol 1000) | 2.5 |
| 9 | Light Liquid Paraffin | 5 |
| 10 | Isopropyl Myristate | 5 |
| 11 | Propylene Glycol | 10 |
| 12 | Methyl Paraben | 0.2 |
| 13 | Propyl Paraben | 0.02 |
| 14 | Disodium Edetate | 0.1 |
| 15 | Disodium hydrogen Orthophosphate anhydrous | 0.5 |
| 16 | Purified Water | 58.5 |

TABLE 4

Formulation of Neomycin Sulphate & Betamethasone Valerate Cream with Chitosan and Docusate Sodium

| S. No | Ingredients | % w/w |
|---|---|---|
| 1 | Neomycin Sulphate | 0.5 |
| 2 | Betamethasone Valerate | 0.12 |
| 3 | Docusate Sodium | 1 |
| 4 | Chitosan | 0.25 |
| 5 | Lactic acid | 0.1 |
| 6 | Cetostearyl Alcohol | 8.25 |
| 7 | White Soft Paraffin | 8.25 |
| 8 | Polyoxyl 20cetostearyl ether (Cetomacrogol 1000) | 2.5 |
| 9 | Light Liquid Paraffin | 5 |
| 10 | Isopropyl Myristate | 5 |
| 11 | Propylene Glycol | 10 |
| 12 | Methyl Paraben | 0.2 |
| 13 | Propyl Paraben | 0.02 |
| 14 | Disodium Edetate | 0.1 |
| 15 | Disodium hydrogen Orthophosphate anhydrous | 0.5 |
| 16 | Purified Water | 58.5 |

Figure 1:
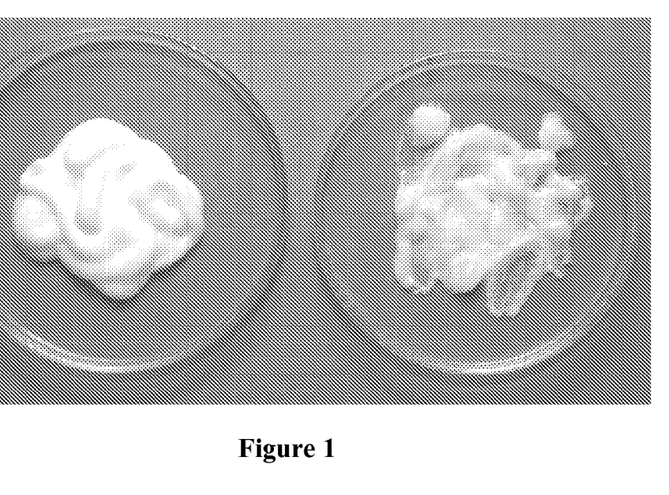
FIG. 1—Non-homogeneous nature of creams containing chitosan with non-compatible excipient such as carbomer FIG. 2—Film formation using chitosan

The above products (tables 1 to 5) are examples of products that do not form homogeneous creams, and produce non-homogeneous creams of the type illustrated in FIG. 1. Yet the proportions stated in these examples are some things that a person skilled in the art may use based on currently available knowledge. Only after a thorough and extensive trials and errors would it is possible to arrive at right types and proportions of excipients.

As we have discussed earlier, in a combination therapy, steroids like Betamethasone Valerate provide relief against inflammation and antibacterial like Neomycin Sulphate provide relief against bacterial infections. However, the aspects such as like skin protection, bleeding at the site, mobility of pathogens from one site to another, etc are not addressed so far in a single dose therapy.

This present invention with its single-dose application fills this gap by incorporating chitosan and tapping the required benefits of skin protection (by way of film forming property), stopping the bleeding (by way of blood clotting property) and immobilization of pathogenic microbes (due to its cationic electrostatic property).

Therapeutic value addition by incorporation of a functional excipient in the form of a chitosan which is a biopolymer in the cream matrix. The value addition is an integrated sub-set of the following functional attributes of the biopolymer:
 formulation of a micro-film on the skin surface
 accelerated blood clotting as compared to creams that do not contain film-forming biopolymers
 electrostatic immobilisation of surface microbes due to cationic charge of the biopolymer
 significant enhancement of the skin epithelisation or regeneration The inventive efforts involved in developing the platform technology covered by incorporation of a functional biopolymer in prescription dermaceutical products are:
 in identification of the complementary therapeutic value that such incorporation delivers
 in identification of issues related to physio-chemical stability of the product resulting from the incorporation of the biopolymer
 in providing a single dose format where the bacterial infection and inflammation has been identified The importance of a single dose treatment, particularly in the underdeveloped countries cannot be overemphasized. In absence of access to a general physician in most parts of south Asia or Africa, let alone a skin specialist, a single dose formulation dramatically increases chances of eliminating root cause of the skin disorder while also allowing the skin to regenerate.

During dermatological conditions, currently available therapies do not address the issues like protecting the skin, arresting the bleeding etc. The unique innovative formulation of the present invention takes care of the skin conditions by treating them along with controlling the superficial bleeding at the site. It is well understood that if the superficial bleeding is left untreated, it will lead to secondary microbial infections. The present invention advantageously provides a solution to this unmet need.

Further, with ever increasing pressures on medical support systems and the attendant scarcity/high cost of the same, there is an emergent need all across the globe to address the following issues in such cases—

Patients waiting too long for treatment
Staying unnecessarily long when they get to hospital
Having to come back more often than they need to
Reducing the length of stay is a key underlying problem to be tackled in most cases. The present invention with its single-dose therapy reduces the overall treatment time of a serious skin disorder significantly.

Preferred Embodiment 1

A novel dermaceutical cream for topical treatment of bacterial skin infections, inflammations, and for related wound healing, wherein said cream comprises an antibacterial agent, Neomycin Sulphate, a corticosteroid, Betamethasone Valerate and a biopolymer provided in a cream base, said cream base comprising at least one of each of a preservative, a primary and a secondary emulsifier, a waxy material, a co-solvent, an acid, and water, preferably purified water.

Embodiment no. 1: A novel dermaceutical cream as disclosed in the preferred embodiment no. 1, wherein said cream further comprising any of a group comprising a buffering agent, an antioxidant, a chelating agent, a humectant, or any combination thereof.

Embodiment no. 2: A novel dermaceutical cream as disclosed in the preferred embodiment no. 1 wherein said antibacterial agent Neomycin Sulphate is added in an amount between about 0.05% w/w and about 5% w/w, preferably between 0.1 and 1.0% w/w, more preferably 0.5 w/w; and said corticosteroid Betamethasone Valerate is added in an amount between about 0.001% (w/w) and about 5% (w/w), preferably between 0.05% and about 2.5% w/w, more preferably 0.12 w/w and, said biopolymer is in the form of chitosan, added in an amount between 0.01% and about 1% by weight, preferably added in an amount from about 0.01% w/w to about 0.5% w/w and most preferably about 0.25% w/w, said chitosan being US Pharmacopoeia conformant with regard to its functional excipient category and selected from any grades such as Long Chain, Medium Chain & Short Chain, and has a molecular weight in the range between 50 kDa to 5000 kDa, said primary and secondary emulsifiers are selected from a group comprising Cetostearyl alcohol, Cetomacrogol-1000, Polysorbate-80, Span-80, and the like and added in an amount from about 1% (w/w) to 20% (w/w); said waxy materials is selected from a group comprising white soft paraffin, liquid paraffin, hard paraffin and the like, or any combination thereof, and added in an amount from about 5% (w/w) to 30% (w/w); said co-solvent is selected from a group comprising Propylene Glycol, Hexylene Glycol, PolyEthylene Glycol-400, Isopropyl Myristate and the like, or any combination thereof, and added in an amount from about 5% (w/w) to 50% (w/w); said acid is selected from a group comprising HCl, $H_2SO_4$, $HNO_3$, Lactic acid and the like, or any combination thereof, and added in an amount from about 0.005% (w/w) to 0.5% (w/w); said preservative is selected from a group comprising Methylparaben, Propylparaben, Chlorocresol, Potassium sorbate, Benzoic acid and the like, or any combination thereof, and added in an amount from about 0.05% (w/w) to 0.5% (w/w); said water is added in the amount in the range of 20% (w/w) to 75% (w/w), preferably 45% (w/w) to 65% (w/w), more preferably 55% (w/w) to 62% (w/w), preferably purified water.

Embodiment no. 3: A novel cream as disclosed in the preferred embodiment no. 1 and the embodiment no. 2, further comprising a buffering agent which is selected from a group comprising Di Sodium Hydrogen Ortho Phosphate, Sodium Hydrogen Ortho Phosphate and the like, or any combination thereof, and added in an amount from about 0.05% (w/w) to 1.00% (w/w).

Embodiment no. 4: A novel cream as disclosed in the preferred embodiment no. 1 and the embodiments no. 2 and 3, further comprising an antioxidant which is selected from a group comprising Butylated Hydroxy Anisole, Butylated Hydroxy Toluene and the like, or any combination thereof, and added in an amount from about 0.05% (w/w) to 5% (w/w).

Embodiment no. 5: A novel cream as disclosed in the preferred embodiment no. 1 and the embodiments no. 2 to 4, further comprising a chelating agent which is selected from a group comprising Disodium EDTA and the like, or any combination thereof, and added in an amount from about 0.05% (w/w) to 1% (w/w).

Embodiment no. 6: A novel cream as disclosed in the preferred embodiment no. 1 and the embodiments no. 2 to 4, further comprising a humectant which is selected from a group comprising Glycerin, Sorbitol, and the like, or any combination thereof, and added in an amount from about 5% (w/w) to 50% (w/w).

Embodiment no. 7: A process of making a cream is disclosed, said process comprising the steps of providing an antibacterial agent, Neomycin Sulphate, a corticosteroid, Betamethasone Valerate, and a biopolymer in a cream base comprising at least one of each of a preservative, a primary and a secondary emulsifier, a waxy material, a co-solvent, an acid, and water, preferably purified water, and mixing all the ingredients together to form a homogeneous cream.

Embodiment no. 8: A process of making a cream as disclosed in the embodiment no. 7, wherein the ingredients further comprise any of a group comprising a buffering agent, an antioxidant, a chelating agent, a humectant, or any combination thereof.

Embodiment no. 9: A novel cream as disclosed in any of the foregoing embodiments, wherein chitosan has a molecular weight range of 1 kdal to 5000 kdal.

The present invention will be further elucidated with reference to the accompanying examples containing the composition and stability studies data, which are however not intended to limit the invention in any way whatever.

Example-I

TABLE 6

Neomycin Sulphate (0.5%) + Betamethasone Valerate (0.12%) + Chitosan Cream

| S. No | Ingredients | % w/w |
|---|---|---|
| 1 | Neomycin Sulphate | 0.5 |
| 2 | Betamethasone Valerate | 0.12 |
| 3 | Chitosan | 0.25 |
| 4 | Lactic acid | 0.1 |
| 5 | Cetostearyl Alcohol | 8.25 |
| 6 | White Soft Paraffin | 8.25 |
| 7 | Polyoxyl 20cetostearyl ether (Cetomacrogol 1000) | 2.5 |
| 8 | Light Liquid Paraffin | 5 |
| 9 | Isopropyl Myristate | 5 |
| 10 | Propylene Glycol | 10 |
| 11 | Methyl Paraben | 0.2 |
| 12 | Propyl Paraben | 0.02 |
| 13 | Disodium Edetate | 0.1 |
| 14 | Disodium hydrogen Orthophosphate anhydrous | 0.5 |
| 15 | Purified Water | 59.5 |

A comparison of table 6, and tables 1 to 5 will illustrate the difference in the products that would be based on the conventional drug design and the innovative approach adopted in the present invention.

APIs-stability experiments were carried out (see tables 7-9) using the product of the present invention. Tests were carried out to observe (or measure as appropriate) the physical appearance of the product, the pH value and assay of the APIs over a period of time. Each gram of product of the present invention used for the tests contained appropriate amount of steroid—Betamethasone Valerate and antibacterial—Neomycin Sulphate.

The product used for the Stability Studies tests contained approximately 10% extra APIs (overages). It was packaged in an aluminum collapsible tube.

Detailed test results for the product have been presented. The % of the corticosteroid, Betamethasone Valerate and the antibacterial, Neomycin Sulphate used in all examples are measured w/w with respect to the final product.

PRODUCT: Betamethasone Valerate+Neomycin Sulphate Cream

PACK: Aluminum Collapsible tube

Composition: Each gm contains: i) Betamethasone Valerate IP 0.12% w/w
ii) Neomycin Sulphate IP 0.5% w/w

TABLE 7

Description Test, Batch No. BNC-03
Measured parameter: Physical appearance;
Best value of measured parameter:
Homogeneous White to off White Viscous cream
Method of measurement: Observation by naked eye

| | Initial | 1st Month | 2nd Month | 3rd Month |
|---|---|---|---|---|
| 40° C. 75% RH | Homogenous White to off White viscous cream | Homogenous White to off White viscous cream | Homogenous White to off White viscous cream | Homogenous White to off White viscous cream |
| 30° C. 65% RH | | Do | Do | Do |
| 25° C. 60% RH | | Do | Do | Do |
| Temp cycling | | Do | — | — |
| Freezthaw | | Do | — | — |

TABLE 8 pH Test, Batch No. BNC-03
Measured parameter: pH; Limits of measured parameter: 3-6
Method of measurement: Digital pH Meter

| | Initial | 1st Month | 2nd Month | 3rd Month |
|---|---|---|---|---|
| 40° C. 75% RH | 5.03 | 5.03 | 5.03 | 5.02 |
| 30° C. 65% RH | — | 5.03 | 5.03 | 5.03 |
| 25° C. 60% RH | — | 5.05 | 5.03 | 5.02 |
| Temp cycling | — | 5.03 | — | — |
| Freezthaw | — | 5.02 | — | — |

TABLE 9

Assay (%) Test, Batch No. BNC-03
Measured parameter: Assay (%) Limits of measured parameter: 90-110
Method of measurement: HPLC Method

| Conditions | Assay (%) | Initial | 1st Month | 2nd Month | 3rd Month |
|---|---|---|---|---|---|
| 40° C. 75% RH | i) Betamethasone Valerate | 107.57 | 107.46 | 107.16 | 107.11 |
| | ii) Neomycin Sulphate | 108.56 | 108.51 | 108.32 | 108.11 |
| 30° C. 65% RH | i) Betamethasone Valerate | — | 107.53 | 107.41 | 107.36 |
| | ii) Neomycin Sulphate | | 108.48 | 108.42 | 108.20 |
| 25° C. 60% RH | i) Betamethasone Valerate | — | 107.54 | 107.42 | 107.40 |
| | ii) Neomycin Sulphate | | 108.54 | 108.42 | 108.21 |
| Temp cycling | i) Betamethasone Valerate | — | 107.53 | — | — |
| | ii) Neomycin Sulphate | | 108.51 | — | — |
| Freezthaw | i) Betamethasone Valerate | — | 107.01 | — | — |
| | ii) Neomycin Sulphate | | 107.25 | — | — |

Method of Application of the Cream:

The cream is applied after thorough cleansing and drying the affected area. Sufficient cream should be applied to cover the affected skin and surrounding area. The cream should be applied two-four times a day depending upon the skin conditions for the full treatment period, even though symptoms may have improved.

Experiments:

Experiments were carried out with the cream in laboratory as well as using suitable animal models inflicted with excision wounds. Four aspects were tested—wound contraction, epithelisation, blood clotting time, and film forming. These aspects together would suggest that the microbes were immobilized thereby leading to effective wound healing.

A. Wound Contraction:

Excision wound healing activity of the cream of the present invention was determined through animal testing. An excision wound 2.5 cm in diameter was inflicted by cutting away full thickness of the skin. The amount of contraction of the wound observed over a period indicated that the cream of present invention provides significantly improved wound contraction than that achieved through application of a conventional cream.

B. Period of Epithelisation:

Epithelisation of the wound occurred within shorter number of days using the cream of the present invention as compared to the days taken for epithelisation using the conventional cream Therefore one benefit of the cream of the present invention is that it facilitates faster epithelisation of the skin than through the use of conventional creams.

C. Blood Clotting:

Blood clotting time was observed in both groups of animals, untreated control group and the test group of animals treated with the product of the present invention. Statistically significant decrease in the blood clotting time in treated group animals was observed when compared with that of the control group animals. The mean percent reduction of 35-40% was observed for the blood clotting time using the product of the present invention.

Film Forming Properties:

It is evident from FIG. 1 that chitosan does not lose its film forming property in the presence of the excipients used for cream preparations in the present invention.

Results and Discussion:

It is evident that the properties of chitosan when used in formulations containing the excipients used in the current invention are not compromised in any way. This has been achieved through a careful selection of excipients. For example, our experiments show that widely used excipients such as xanthan gum or carbomer precipitate in combination with chitosan due to cationic, anionic interactions.

The therapeutic impact, as observed from the animal testing, of the addition of chitosan to corticosteroid, Betamethasone Valerate & antibacterial agent, Neomycin Sulphate is shown in the following table by considering various aspects of therapeutic cure of a compromised skin condition:

TABLE 10

Figure 2:
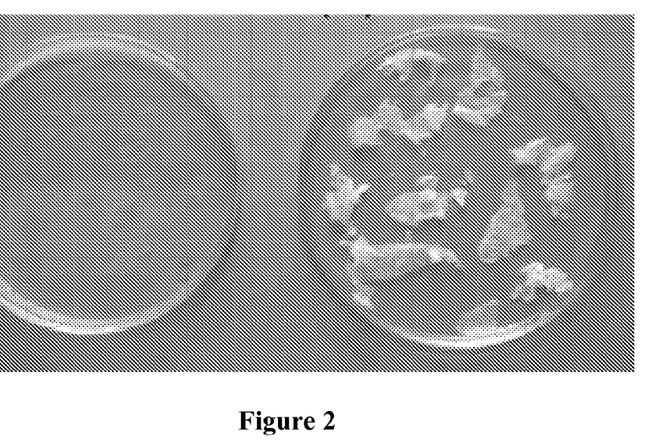

| Therapeutic aspect | Existing creams | Products of the present invention |
|---|---|---|
| 1. Blood Clotting time | None explicitly claimed | Statistically significant reduction in clotting time as evidenced by pre-clinical animal trials |
| 2. Immobilisation of microbes | None explicitly claimed | Expected to immobilise the surface microbes because of the cationic charge of chitosan |
| 3. Epidermal growth support | None explicitly claimed | It is well known that chitosan possesses properties that have significant complimentary action on epidermal growth. This functional aspect of chitosan is preserved in the product of the present invention |
| 4. Micro-film | None explicitly forming | Yes (see FIG. 2) claimed |
| 5. Overall wound healing medicinal effect | Standard as per existing products | Provides superior healing properties |

It is evident that the film forming ability of the chitosan incorporated in the cream allows better access of the antibacterial agent, Neomycin Sulphate and the corticosteroid, Betamethasone Valerate to the infected area and results in better functioning of these APIs.

The therapeutic efficacy of topically applied cream of the present invention is due to the pronounced antibacterial activity of the Neomycin Sulphate against the organisms responsible for skin infections, the antiallergic & anti-inflammatory property of corticosteroid, Betamethasone Valerate, the unique ability of actives to penetrate intact skin and wound healing & soothing properties of chitosan.

It is evident from the foregoing discussion that the present invention offers the following advantages and unique aspects over the currently available dermaceutical compositions for bacterial infections & inflammations:

1. The cream of the present invention incorporates a skin-friendly biopolymer in the form of chitosan provides enhanced therapeutic outcomes. This is evident from the reduced blood clotting time, increased epithelial effect, and faster relief from infection and inflammation.

2. The cream of the present invention incorporates a biopolymer without compromising the stability of the cream matrix and without adversely affecting the functioning of known active pharmaceutical ingredients. This has been achieved through a careful selection of functional excipients to bypass undesirable aspects of physio-chemical compatibility/stability and bio-release.

3. The cream of the present invention provides an integrated uni-dose or a single-dose therapy hitherto unavailable in prescription dermaceutical formulations.

4. The novel cream of the present invention is adequately stable/efficacious at ambient conditions and does not need special temperature control during transportation/storage—hence will go a long way in achieving these social objectives.

According to another embodiment of the present invention, there is also provided a process for treating bacterial skin infections, skin inflammations, and wound healing involving contacting human skin with the above-disclosed composition.

While the above description contains much specificity, these should not be construed as limitation in the scope of the invention, but rather as an exemplification of the preferred embodiments thereof. It must be realized that modifications and variations are possible based on the disclosure given above without departing from the spirit and scope of the invention. Accordingly, the scope of the invention should be determined not by the embodiments illustrated, but by the appended claims and their legal equivalents.

We claim:

1. A medicinal cream for topical treatment of bacterial skin infections, inflammations, and for related wound healing, wherein said cream comprises an antibacterial agent, Neomycin Sulphate, a corticosteroid, Betamethasone Valerate and a biopolymer in the form of chitosan provided in a cream base, said cream base comprising at least one of each of a preservative, a primary and a secondary emulsifier, a waxy material, a co-solvent, an acid, and water.

2. A medicinal cream as claimed in claim 1, wherein said cream further comprising any of a group comprising a buffering agent, an antioxidant, a chelating agent, a humectant, or any combination thereof.

3. A medicinal cream as disclosed in claim 1 wherein:
said antibacterial agent Neomycin Sulphate being in an amount about 0.05% w/w and about 5% w/w, and
said corticosteroid Betamethasone Valerate being in an amount between about 0.001% (w/w) and about 5% (w/w), about 0.12% w/w, and
said chitosan being in an amount between about 0.01% and about 1% by weight,
said primary and secondary emulsifiers are selected from a group comprising Cetostearyl alcohol, Cetomacrogol-1000, Polysorbate-80, Span-80 and being in an amount from about 1% (w/w) to 20% (w/w); said waxy materials is selected from a group comprising white soft paraffin, liquid paraffin, hard paraffin, or any combination thereof, and being in an amount from about 5% (w/w) to 30% (w/w); said co-solvent is selected from a group comprising Propylene Glycol, Hexylene Glycol, Poly-Ethylene Glycol-400, Isopropyl Myristate, or any combination thereof, and being in an amount from about 5% (w/w) to 50% (w/w); said acid is selected from a group comprising HCl, $H_2SO_4$, $HNO_3$, Lactic acid, or any combination thereof, and being in an amount from about 0.005% (w/w) to 0.5% (w/w); said preservative is selected from a group comprising Methylparaben, Propylparaben, Chlorocresol, Potassium sorbate, Benzoic acid, or any combination thereof, and being in an amount from about 0.05% (w/w) to 0.5% (w/w); said water being in the amount 55% (w/w) to 62% (w/w).

4. A novel medicinal cream as claimed in claims 1 or 3 further comprising a buffering agent which is selected from a group comprising Di Sodium Hydrogen Ortho Phosphate, Sodium Hydrogen Ortho Phosphate, or any combination thereof, and being in an amount from about 0.05% (w/w) to 1.00% (w/w).

5. A novel medicinal cream as claimed in claims 1 or 3 further comprising an antioxidant which is selected from a group comprising Butylated Hydroxy Anisole, Butylated Hydroxy Toluene, or any combination thereof, and being in an amount from about 0.05% (w/w) to 5% (w/w).

6. A novel medicinal cream as claimed in claims 1 or 3 further comprising a chelating agent which is selected from a group comprising Disodium EDTA, or any combination thereof, and being in an amount from about 0.05% (w/w) to 1% (w/w).

7. A novel medicinal cream as claimed in claims 1 or 3 further comprising a humectant which is selected from a group comprising Glycerin, Sorbitol, or any combination thereof, and being in an amount from about 5% (w/w) to 50% (w/w).

8. A process of making a cream, said process comprising the steps of providing an antibacterial agent, a corticosteroid, and a biopolymer in a cream base comprising at least one of each of a preservative, a primary and a secondary emulsifier, a waxy material, a co-solvent, an acid, and water and mixing all the ingredients together to form a homogeneous cream.

9. A process of making a cream as claimed in claim 8, wherein the ingredients further comprise any of a group comprising a buffering agent, an antioxidant, a chelating agent, a humectant, or any combination thereof.

* * * * *